United States Patent
Turksoy

(10) Patent No.: US 11,864,892 B2
(45) Date of Patent: Jan. 9, 2024

(54) METHODS AND SYSTEMS FOR REDUCING DIFFERENCE BETWEEN CALCULATED AND MEASURED ANALYTE LEVELS

(71) Applicant: Senseonics, Incorporated, Germantown, MD (US)

(72) Inventor: Kamuran Turksoy, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 363 days.

(21) Appl. No.: 17/105,198

(22) Filed: Nov. 25, 2020

(65) Prior Publication Data

US 2021/0153785 A1    May 27, 2021

Related U.S. Application Data

(60) Provisional application No. 62/941,083, filed on Nov. 27, 2019.

(51) Int. Cl.

| | |
|---|---|
| A61B 5/1455 | (2006.01) |
| A61B 5/1495 | (2006.01) |
| A61B 5/145 | (2006.01) |
| A61B 5/01 | (2006.01) |
| G16H 10/40 | (2018.01) |
| G16H 40/40 | (2018.01) |
| A61B 5/151 | (2006.01) |
| A61B 5/00 | (2006.01) |
| A61B 5/1459 | (2006.01) |

(52) U.S. Cl.
CPC .............. *A61B 5/1495* (2013.01); *A61B 5/01* (2013.01); *A61B 5/1455* (2013.01); *A61B 5/14532* (2013.01); *G16H 10/40* (2018.01); *G16H 40/40* (2018.01); *A61B 5/0004* (2013.01); *A61B 5/1459* (2013.01); *A61B 5/151* (2013.01); *A61B 2562/162* (2013.01)

(58) Field of Classification Search
CPC .............. A61B 5/1455; A61B 5/14551; A61B 5/14552; A61B 5/14532
See application file for complete search history.

(56) References Cited

U.S. PATENT DOCUMENTS

| | | |
|---|---|---|
| 2011/0231105 A1 | 9/2011 | Wu et al. |
| 2012/0283542 A1 | 11/2012 | McGarraugh |
| 2015/0087942 A1 | 3/2015 | Brauker et al. |
| 2016/0139043 A1 | 5/2016 | Gulati et al. |
| 2016/0183854 A1 | 6/2016 | Lee |
| 2019/0094233 A1 | 3/2019 | Chen et al. |

*Primary Examiner* — Marjan Fardanesh
(74) *Attorney, Agent, or Firm* — Rothwell, Figg, Ernst & Manbeck, P.C.

(57) ABSTRACT

Systems, methods, and apparatuses for reducing error between calculated analyte levels and impractical analyte measurements using practical analyte measurements as reference measurements for calibration. Reducing the error may include converting a practical reference analyte measurement into an estimated impractical analyte level, updating a conversion function using the estimated impractical analyte level, and using the updated conversion function to calculate an analyte level. In some embodiments, the practical reference analyte measurement may be a capillary blood analyte measurement, and the estimated impractical analyte level may be an estimated venous blood analyte level. In some embodiments, the updated conversion function may minimize the error between analyte levels calculated using the updated conversion function and estimated venous blood analyte levels.

30 Claims, 6 Drawing Sheets

US 11,864,892 B2

METHODS AND SYSTEMS FOR REDUCING DIFFERENCE BETWEEN CALCULATED AND MEASURED ANALYTE LEVELS

CROSS-REFERENCE TO RELATED APPLICATION

The present application claims the benefit of priority to U.S. Provisional Application Ser. No. 62/941,083, filed on Nov. 27, 2019, which is incorporated herein by reference in its entirety.

BACKGROUND

Field of Invention

The present invention relates to analyte monitoring systems and methods. More specifically, aspects of the present invention relate to reducing the error between calculated analyte levels and impractical analyte measurements using practical analyte measurements as reference measurements for calibration. Even more specifically, aspects of the present invention relate to reducing the error between calculated blood analyte levels and venous blood analyte measurements using capillary blood analyte measurements as reference measurements for calibration.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels<7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations. In particular, improved calibration systems and methods are needed for more accurate analyte monitoring.

SUMMARY

One aspect of the invention may provide a system including an analyte sensor and a transceiver. The transceiver may be configured to receive first sensor data from the analyte sensor. The transceiver may be configured to calculate a first analyte level using a conversion function and the first sensor data. The transceiver may be configured to receive a reference analyte measurement. The transceiver may be configured to convert the reference analyte measurement into an estimated analyte level. The transceiver may be configured to update the conversion function using the estimated analyte level as a calibration point. The transceiver may be configured to receive second sensor data from the analyte sensor. The transceiver may be configured to use the updated conversion function and the second sensor data to calculate a second analyte level.

In some aspects, the reference analyte measurement may be a capillary blood analyte measurement, and the estimated analyte level may be an estimated venous blood analyte level. In some aspects, the updated conversion function may minimize the error between analyte levels calculated using the updated conversion function and estimated venous blood analyte levels.

In some aspects, the reference analyte measurement may be a self-monitoring blood glucose (SMBG) measurement obtained from a finger-stick blood sample.

In some aspects, the conversion of the reference analyte measurement into the estimated analyte level may be based on a model of differences between capillary blood analyte level measurements and venous blood analyte level measurements. In some aspects, the conversion of the reference analyte measurement into the estimated analyte level may be based on a cost function that maximizes the likelihood of a fit of the error between calculated analyte levels and capillary blood analyte level measurements to the model of the differences between the capillary blood analyte level measurements and the venous blood analyte level measurements. In some aspects, the conversion of the reference analyte measurement into the estimated analyte level may be based on a cost function minimizes the negative likelihood of a fit of the error between calculated analyte levels and capillary blood analyte level measurements to the model of the differences between the capillary blood analyte level measurements and the venous blood analyte level measurements.

In some aspects, the first analyte level may be a second medium analyte level, and calculating the first analyte level using the conversion function and the first sensor data may include: calculating a first medium analyte level using at least the first sensor data; calculating a first medium analyte level rate of change using at least the first medium analyte level; and calculating the second medium analyte level using at least the first medium analyte level and first medium analyte level rate of change. In some aspects, the first medium may be interstitial fluid, and the second medium may be blood.

In some aspects, the first sensor data may include light and temperature measurements.

In some aspects, the transceiver may be further configured to: display the calculated first analyte level and display the calculated second analyte level. In some aspects, displaying the calculated first analyte level may include displaying the calculated first analyte level on a display of the transceiver, and displaying the calculated second analyte level may include displaying the calculated second analyte level on the display of the transceiver. In some aspects, displaying the calculated first analyte level may include conveying the calculated first analyte level to a display device, and displaying the calculated second analyte level may include conveying the calculated second analyte level to the display device. In some aspects, the system may further include the display device, and the display device may be configured to: receive and display the calculated first analyte level and receive and display the calculated second analyte level.

In some aspects, the transceiver may be further configured to: receive an updated error model; receive a second reference analyte measurement; convert the second reference analyte measurement into a second estimated analyte level using the updated error model; update the conversion function using the second estimated analyte level as a calibration point; receive third sensor data from the analyte sensor; and use the twice updated conversion function and the third sensor data to calculate a third analyte level.

Another aspect of the invention may provide a method including using a transceiver to receive first sensor data from an analyte sensor. The method may include using the transceiver to calculate a first analyte level using a conversion function and the first sensor data. The method may include using the transceiver to receive a reference analyte measurement. The method may include using the transceiver to convert the reference analyte measurement into an estimated analyte level. The method may include using the transceiver to update the conversion function using the estimated analyte level as a calibration point. The method may include using the transceiver to receive second sensor data from the analyte sensor. The method may include using the transceiver to calculate a second analyte level using the updated conversion function and the second sensor data.

In some aspects, the reference analyte measurement may be a capillary blood analyte measurement, and the estimated analyte level may be an estimated venous blood analyte level. In some aspects, the updated conversion function may minimize the error between analyte levels calculated using the updated conversion function and estimated venous blood analyte levels.

In some aspects, the reference analyte measurement may be a self-monitoring blood glucose (SMBG) measurement obtained from a finger-stick blood sample.

In some aspects, the conversion of the reference analyte measurement into the estimated analyte level may be based on a model of differences between capillary blood analyte level measurements and venous blood analyte level measurements. In some aspects, the conversion of the reference analyte measurement into the estimated analyte level may be based on a cost function that maximizes the likelihood of a fit of the error between calculated analyte levels and capillary blood analyte level measurements to the model of the differences between the capillary blood analyte level measurements and the venous blood analyte level measurements. In some aspects, the conversion of the reference analyte measurement into the estimated analyte level may be based on a cost function minimizes the negative likelihood of a fit of the error between calculated analyte levels and capillary blood analyte level measurements to the model of the differences between the capillary blood analyte level measurements and the venous blood analyte level measurements.

In some aspects, the first analyte level may be a second medium analyte level and calculating the first analyte level using the conversion function, and the first sensor data may include: calculating a first medium analyte level using at least the first sensor data; calculating a first medium analyte level rate of change using at least the first medium analyte level; and calculating the second medium analyte level using at least the first medium analyte level and first medium analyte level rate of change. In some aspects, the first medium may be interstitial fluid, and the second medium may be blood.

In some aspects, the first sensor data may include light and temperature measurements.

In some aspects, the method may further include displaying the calculated first analyte level and displaying the calculated second analyte level. In some aspects, displaying the calculated first analyte level may include displaying the calculated first analyte level on a display of the transceiver, and displaying the calculated second analyte level may include displaying the calculated second analyte level on the display of the transceiver. In some aspects, displaying the calculated first analyte level may include conveying the calculated first analyte level to a display device, and displaying the calculated second analyte level may include conveying the calculated second analyte level to the display device. In some aspects, the method may include: using a display device to receive the calculated first analyte level from the transceiver; using the display device to display the calculated first analyte level; using the display device to receive the calculated second analyte level from the transceiver; and using the display device to display the calculated second analyte level.

In some aspects, the method may further include: using the transceiver to receive an updated error model; using the transceiver to receive a second reference analyte measurement; using the transceiver to convert the second reference analyte measurement into a second estimated analyte level using the updated error model; using the transceiver to update the conversion function using the second estimated analyte level as a calibration point; using the transceiver to receive third sensor data from the analyte sensor; and using the transceiver to use the twice updated conversion function and the third sensor data to calculate a third analyte level.

Another aspect of the invention may provide a transceiver including a sensor interface, a display interface, and a computer. The sensor interface may be configured to receive first sensor data and second sensor data from the analyte sensor. The display interface may be configured to receive a reference analyte measurement from a display device. The computer may include a non-transitory and a processor. The computer may be configured to use a conversion function and the first sensor data to calculate a first analyte level. The computer may be configured to convert the reference analyte measurement into an estimated analyte level. The computer may be configured to update the conversion function using the estimated analyte level as a calibration point. The computer may be configured to use the updated conversion function and the second sensor data to calculate a second analyte level.

In some aspects, the reference analyte measurement may be a capillary blood analyte measurement, and the estimated analyte level may be an estimated venous blood analyte level. In some aspects, the updated conversion function may minimize the error between analyte levels calculated using the updated conversion function and estimated venous blood analyte levels. In some aspects, the reference analyte measurement may be a self-monitoring blood glucose (SMBG) measurement obtained from a finger-stick blood sample.

In some aspects, the conversion of the reference analyte measurement into the estimated analyte level may be based on a model of differences between capillary blood analyte level measurements and venous blood analyte level measurements. In some aspects, the conversion of the reference analyte measurement into the estimated analyte level may be based on a cost function that maximizes the likelihood of a fit of the error between calculated analyte levels and capillary blood analyte level measurements to the model of the differences between the capillary blood analyte level measurements and the venous blood analyte level measurements. In some aspects, the conversion of the reference analyte measurement into the estimated analyte level may be based on a cost function minimizes the negative likelihood of a fit of the error between calculated analyte levels and capillary blood analyte level measurements to the model of the differences between the capillary blood analyte level measurements and the venous blood analyte level measurements.

In some aspects, the first analyte level may be a second medium analyte level, and using the conversion function and the first sensor data to calculate the first analyte level may include: calculating a first medium analyte level using at least the first sensor data; calculating a first medium analyte level rate of change using at least the first medium analyte level; and calculating the second medium analyte level using at least the first medium analyte level and first medium analyte level rate of change. In some aspects, the first medium may be interstitial fluid, and the second medium may be blood.

In some aspects, the first sensor data may include light and temperature measurements. In some aspects, the transceiver may further include a display, and the computer may be further configured to cause the display to: display the calculated first analyte level; and display the calculated second analyte level. In some aspects, the computer may be further configured to cause the display interface to: convey the calculated first analyte level to the display device; and convey the calculated second analyte level to the display device.

In some aspects, the sensor interface may be further configure to receive third sensor data from the analyte sensor. The display interface may be further configured to receive an updated error model and a second reference analyte measurement. The computer may be further configured to: convert the second reference analyte measurement into a second estimated analyte level using the updated error model; update the conversion function using the second estimated analyte level as a calibration point; receive third sensor data from the analyte sensor; and use the twice updated conversion function and the third sensor data to calculate a third analyte level.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
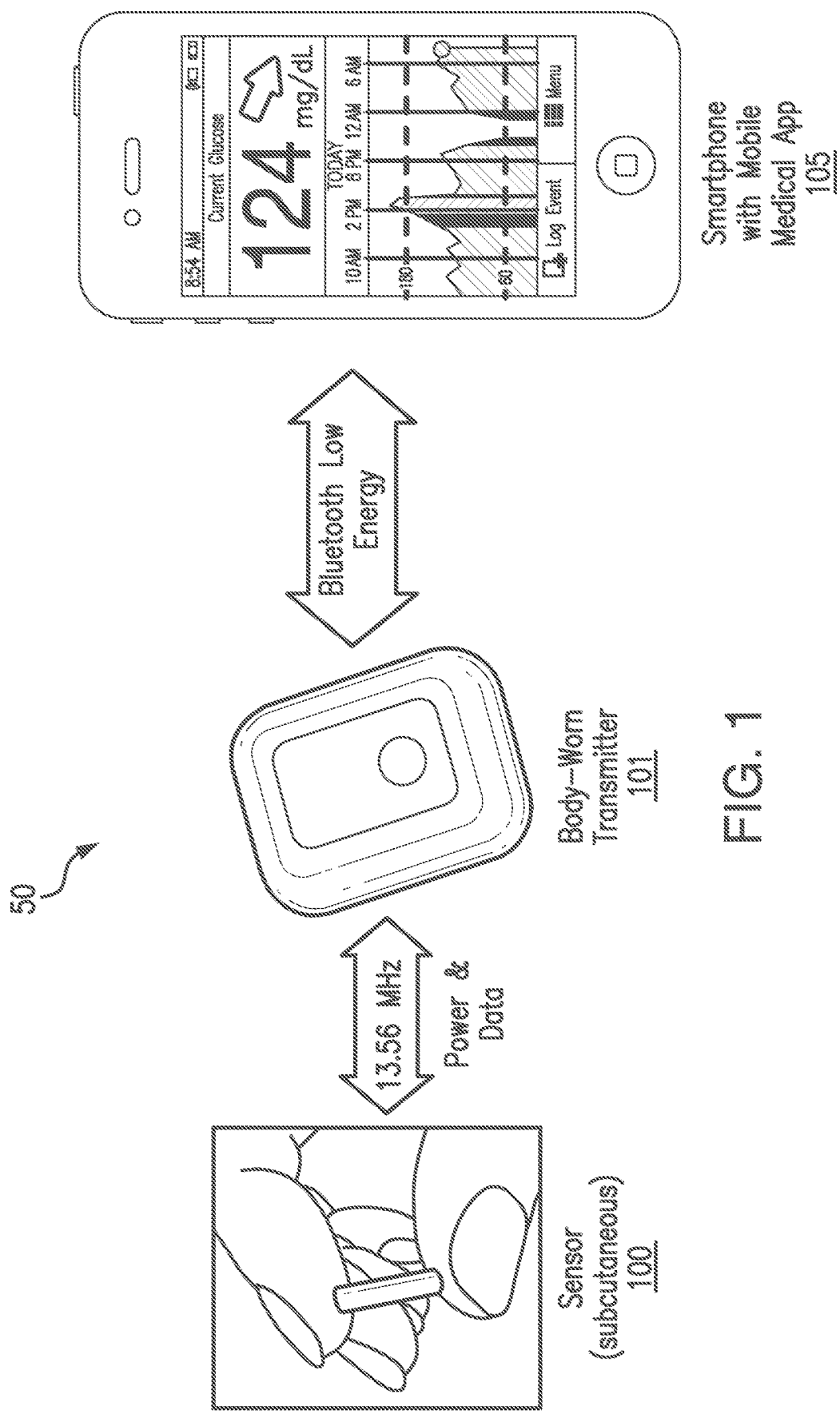
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and a display device 105. In some embodiments, the sensor 100 may be small, fully subcutaneously implantable sensor that measures analyte (e.g., glucose) levels in a medium (e.g., interstitial fluid) of a living animal (e.g., a living human). However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte levels) wirelessly (e.g., via a Bluetooth™ communication standard such as, for example and without limitation Bluetooth Low Energy) to a hand held application running on a display device 105 (e.g., smartphone). In some embodiments, the analyte monitoring system 50 may include a web interface for plotting and sharing of uploaded data.

Figure 2:
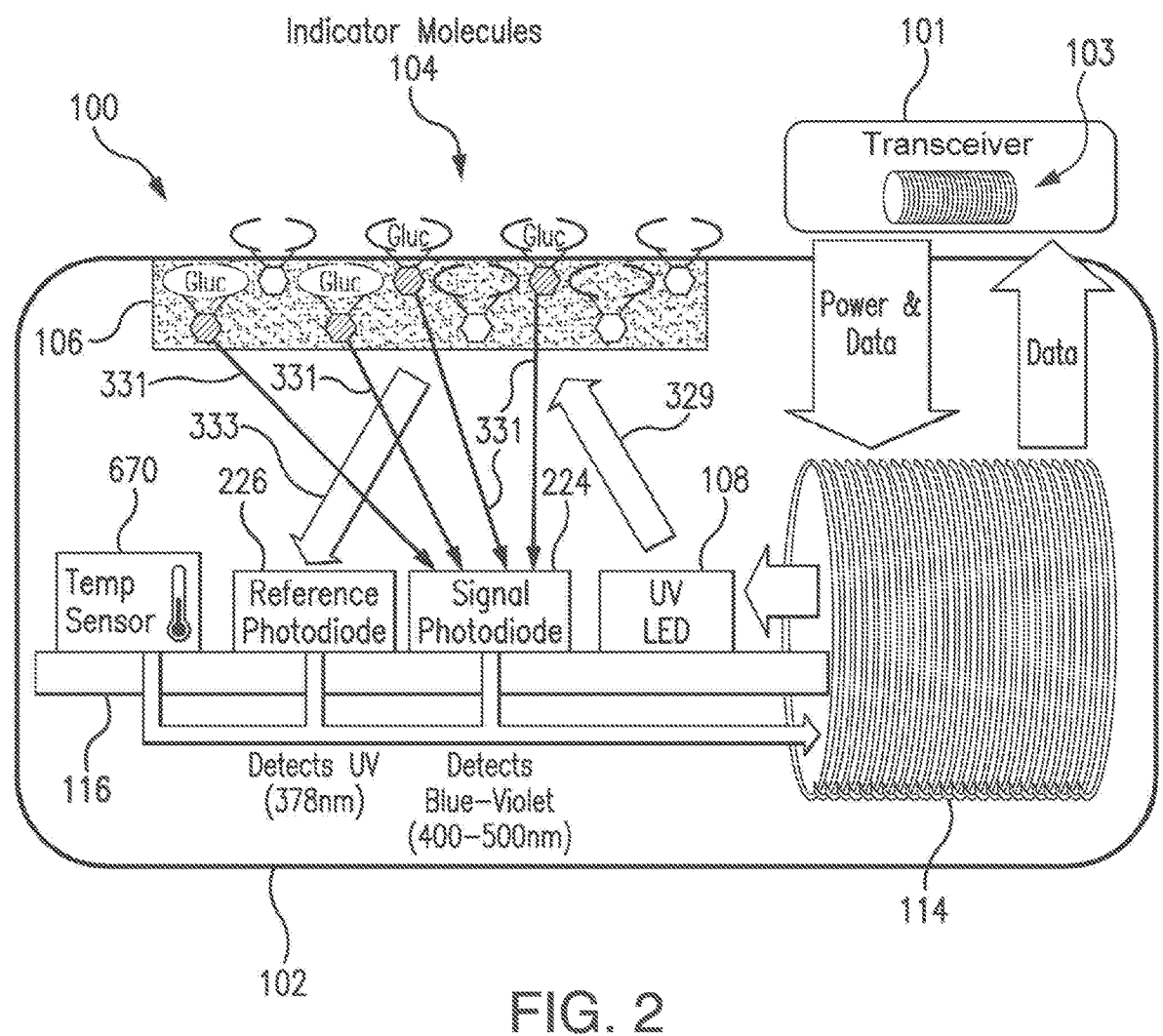
FIG. 2 is a schematic view illustrating a sensor and transceiver of an analyte monitoring system embodying aspects of the present invention.

In some embodiments, as illustrated in FIG. 2, the transceiver 101 may include an inductor 103, such as, for example, a coil. The transceiver 101 may generate an electromagnetic wave or electrodynamic field (e.g., by using a coil) to induce a current in an inductor 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive sensor data (e.g., measurement information) from the sensor 100. For example, in a non-limiting embodiment, the transceiver 101 may receive sensor data by detecting modulations in the electromagnetic wave generated by the sensor 100, (e.g., by detecting modulations in the current flowing through the coil 103 of the transceiver 101).

The inductor 103 of the transceiver 101 and the inductor 114 of the sensor 100 may be in any configuration that permits adequate field strength to be achieved when the two inductors are brought within adequate physical proximity.

In some non-limiting embodiments, as illustrated in FIG. 2, the sensor 100 may be encased in a sensor housing 102 (e.g., body, shell, capsule, or encasement), which may be rigid and biocompatible. The sensor 100 may include an analyte indicator 106, such as, for example, a polymer graft coated, diffused, adhered, or embedded on or in at least a portion of the exterior surface of the sensor housing 102. The analyte indicator 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto is indicative of the level of emission light 331 of the indicator molecules and, thus, the amount or concentration of the analyte of interest (e.g., glucose). In some non-limiting embodiments, one or more of the photodetectors (e.g., photodetector 226) may be sensitive to excitation light 329 that is reflected from the analyte indicator 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductor 114. In some embodiments, the semiconductor substrate 116 and/or a core may provide communication paths between the various secured components.

In some embodiments, the one or more of the sensor housing 102, analyte indicator 106, indicator molecules 104, light source 108, photodetectors 224, 226, temperature transducer 670, substrate 116, and inductor 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductors 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface. In some embodiments where the sensor 100 includes an antenna (e.g., inductor 114), the transceiver interface may include the antenna (e.g., inductor 114) of sensor 100. In some of the transcutaneous embodiments where there exists a wired connection between the sensor 100 and the transceiver 101, the transceiver interface may include the wired connection.

Figure 3:
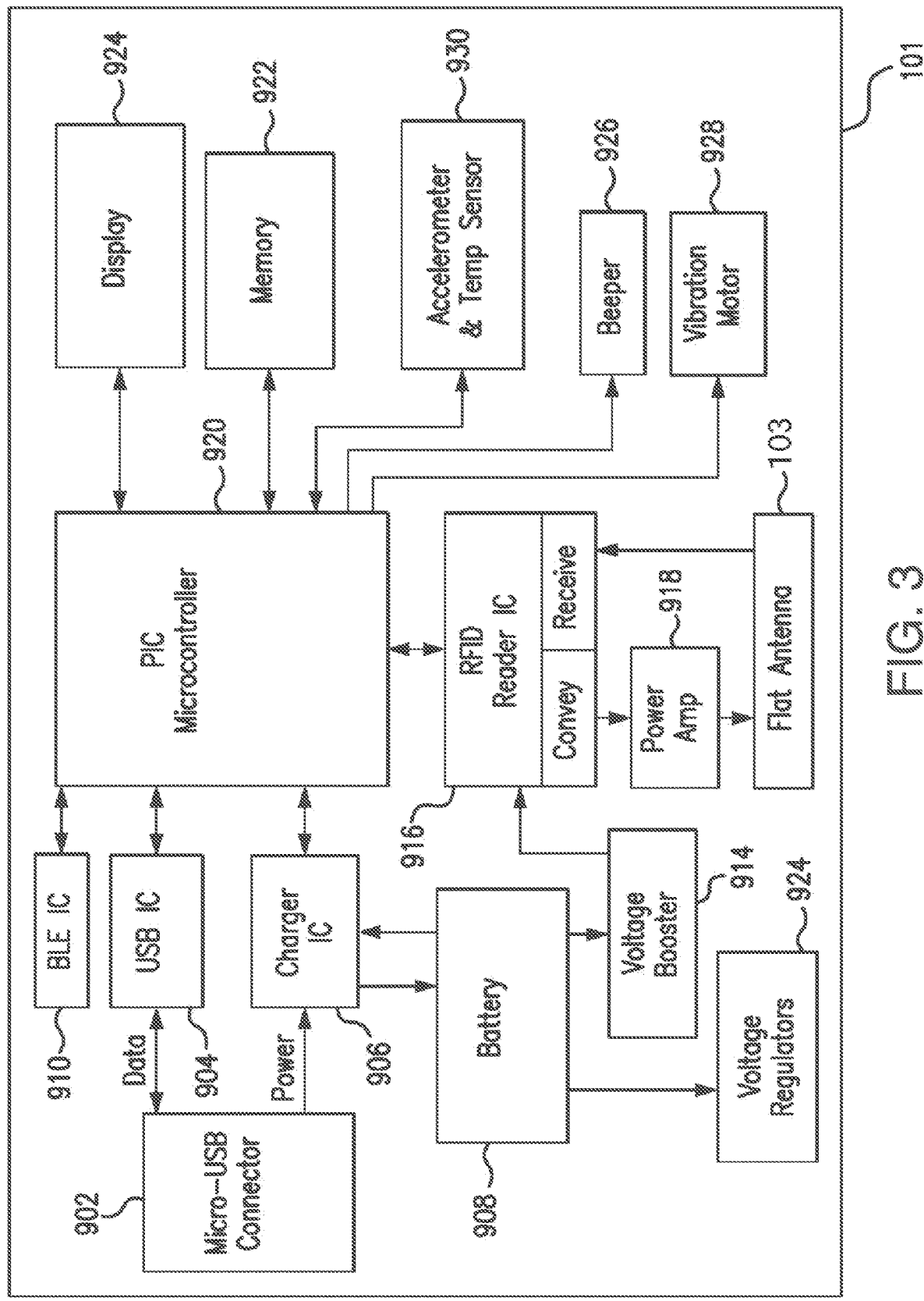
FIG. 3 is a schematic view illustrating a transceiver embodying aspects of the present invention.

FIG. 3 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface, which may enable communication by the transceiver 101 with one or more display devices 105. In some embodiments, the display interface may include the antenna of the wireless communication IC 910 and/or the connector 902. In some non-limiting embodiments, the display interface may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductor 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductor 103 is a flat antenna. In some non-limiting embodiments, the antenna may be flexible. However, as noted above, the inductor 103 of the transceiver 101 may be in any configuration that permits adequate field strength to be achieved when brought within adequate physical proximity to the inductor 114 of the sensor 100. In some embodiments, the transceiver 101 may include a power amplifier 918 to amplify the signal to be conveyed by the inductor 103 to the sensor 100.

The transceiver 101 may include a computer 920 and a memory 922. In some embodiments, the memory 922 (e.g., Flash memory) may be non-volatile and/or capable of being electronically erased and/or rewritten. In some embodiments, the computer 920 may include a processor and a non-transitory memory. In some non-limiting embodiments, the computer 920 may be, for example and without limitation, a peripheral interface controller (PIC) microcontroller. The computer 920 may control the overall operation of the transceiver 101. For example, the computer 920 may control the connector IC 904 or wireless communication IC 910 to transmit data via wired or wireless communication and/or control the RFID reader IC 916 to convey data via the inductor 103. The computer 920 may also control processing of data received via the inductor 103, connector 902, or wireless communication IC 910.

In some embodiments, the transceiver 101 may include a sensor interface, which may enable communication by the transceiver 101 with a sensor 100. In some embodiments, the sensor interface may include the inductor 103. In some non-limiting embodiments, the sensor interface may additionally include the RFID reader IC 916 and/or the power amplifier 918. However, in some alternative embodiments where there exists a wired connection between the sensor 100 and the transceiver 101 (e.g., transcutaneous embodiments), the sensor interface may include the wired connection.

In some embodiments, the transceiver 101 may include a display 924 (e.g., liquid crystal display and/or one or more light emitting diodes), which the computer 920 may control to display data (e.g., analyte levels values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, which may be used in the processing performed by the computer 920.

In some embodiments, the transceiver 101 may be a body-worn transceiver that is a rechargeable, external device worn over the sensor implantation or insertion site. The transceiver 101 may supply power to the proximate sensor 100, calculate analyte levels from data received from the sensor 100, and/or transmit the calculated analyte levels to a display device 105 (see FIG. 1). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2, 5, or 10 minutes) read sensor data and calculate an analyte level and an analyte level trend. From this information, the transceiver 101 may also determine if an alert and/or alarm condition exists, which may be signaled to the user (e.g., through vibration by vibration motor 928 and/or an LED of the transceiver's display 924 and/or a display of a display device 105).

The information from the transceiver 101 (e.g., calculated analyte levels, calculated analyte level trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting embodiments, the MMA may provide alarms, alerts, and/or notifications in addition to any alerts, alarms, and/or notifications received from the transceiver 101. In one embodiment, the MMA may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 of the analyte monitoring system 120 may receive one or more sensor measurements indicative of an amount, level, or concentration of an analyte in a first medium (e.g., interstitial fluid ("ISF")) in proximity to the analyte sensor 100. In some embodiments, the transceiver 101 may receive the sensor measurements from the sensor 100 periodically (e.g., every 1, 2, 5, 10, 15, or 20 minutes). In some embodiments, the one or more sensor measurements may include, for example and without limitation, one or more of (i) one or more measurements indicative of an amount of emission light from indicator molecules 104 of the analyte indicator 106 of the sensor 100 (e.g., as measured by one or more photodetectors 224 of the sensor 100), (ii) one or more measurements indicative of an amount of reference light (e.g., as measured by one or more photodetectors 226 of the sensor 100), and (iii) one or more temperature measurements (e.g., as measured by one or more temperature transducers 670 of the sensor 100). In some embodiments, the transceiver 101 may use the received sensor measurements to calculate a first medium analyte level (e.g., an ISF analyte level or an).

In some embodiments, the transceiver 101 may use the calculated first medium analyte level and at least one or more previously calculated first medium analyte levels to calculate a rate of change of the first medium analyte level ("M1_ROC"). In some non-limiting embodiments, to calculate M1_ROC, the transceiver 101 may use just the calculated first medium analyte level and the most recent previously calculated first medium analyte level and determine M1_ROC as the difference between the calculated first medium analyte level and most recent previously calculated first medium analyte level divided by the time difference between a time stamp for the calculated first medium analyte level and a time stamp for the most recent previously calculated first medium analyte level. In some alternative embodiments, to calculate M1_ROC, the transceiver 101 may use the calculated first medium analyte level and a plurality of the most recent previously calculated first medium analyte levels. In some non-limiting embodiments, the plurality of the most recent previously calculated first medium analyte levels may be, for example and without limitation, the previous two calculated first medium analyte levels, the previous 20 calculated first medium analyte levels, or any number of previously calculated first medium analyte levels in between (e.g., the previous 5 calculated first medium analyte levels). In other alternative embodiments, to calculate M1_ROC, the transceiver 101 may use the calculated first medium analyte level and the previously calculated first medium analyte levels that were calculated during a time period. In some non-limiting embodiments, the time period may be, for example and without limitation, the last one minute, the last 60 minutes, or any amount of time in between (e.g., the last 25 minutes). In some embodiments where the transceiver 101 uses the calculated first medium analyte level and more than one previously calculated first medium analyte levels to calculate M1_ROC, the transceiver 101 may use, for example, linear or non-linear regression to calculate M1_ROC.

In some embodiments, the transceiver 101 may convert the calculated first medium analyte level into a second medium analyte level (e.g., a blood analyte level) by performing a lag compensation, which compensates for the time lag between a second medium analyte level and an first medium analyte level (e.g., the time lag between a blood analyte level and an ISF analyte level). In some embodiments, the transceiver 101 may calculate the second medium analyte level using at least the calculated first medium analyte level and the calculated M1_ROC. In some non-limiting embodiments, the transceiver 101 may calculate the second medium analyte level as $M1\_ROC/p_2+(1+p_3/p_2)*M1\_analyte$, where $p_2$ is analyte diffusion rate, $p_3$ is the analyte consumption rate, and M1_analyte is the calculated first medium analyte level.

In some embodiments, the transceiver 101 may store one or more of the calculated first medium analyte level, calculated M1_ROC, and calculated second medium analyte level (e.g., in memory 922). In some embodiments, the transceiver 101 may convey the calculated first medium analyte level to the display device 105, and the display device 105 may display the calculated first medium analyte level.

In some embodiments, the analyte monitoring system 50 may calibrate the conversion of sensor measurements to second medium (e.g., blood) analyte levels. That is, in some embodiments, the analyte monitoring system 50 may calibrate the manner in which the transceiver 101 calculates second medium analyte levels using the sensor measurements. In some embodiments, the calibration may be performed approximately periodically (e.g., approximately every 12 or 24 hours). In some embodiments, the calibration may be performed using one or more reference measurements. In some embodiments, the one or more references measurements may be capillary blood analyte level measurements (e.g., one or more self-monitoring blood glucose (SMBG) measurements). In some non-limiting embodiments, the display device 105 may prompt a user for one or more reference measurements. In some embodiments, the one or more reference measurements may be entered into the analyte monitoring system 50 using a user interface of the display device 105. In some embodiments, the display device 105 may convey one or more references measurements to the transceiver 101. In some embodiments, the transceiver 101 may receive the one or more reference measurements from the display device 105 and use the one or more reference measurements to perform the calibration.

Figure 4:
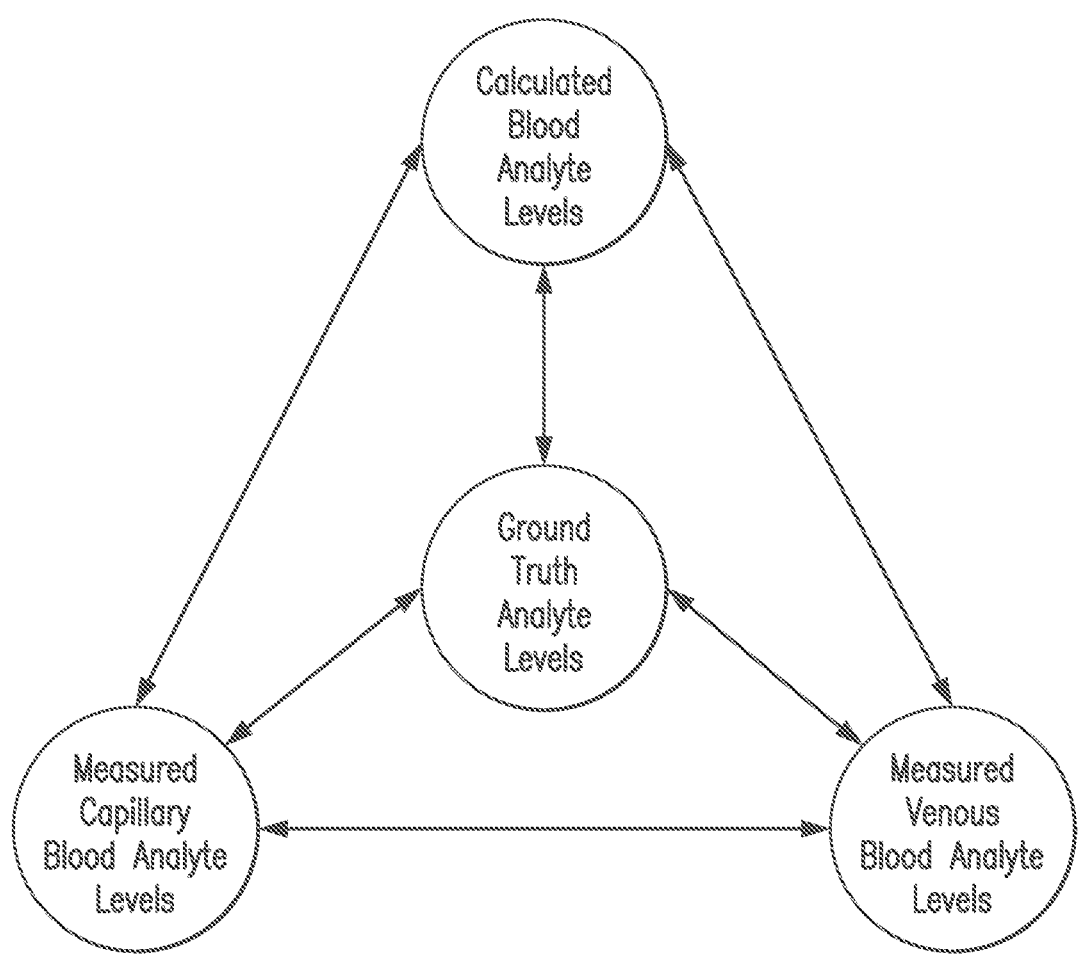
FIG. 4 is an error diagram showing errors between calculated blood analyte levels, capillary blood analyte level measurements, venous blood analyte level measurements, and ground truth blood analyte levels.

In some embodiments, the second medium may be blood, the reference measurements may be capillary blood analyte level measurements, and the transceiver 101 may use sensor measurements received from the sensor 100 to calculate blood analyte levels. FIG. 4 is an error diagram showing errors between each of (i) blood analyte levels calculated by the transceiver 101, (ii) capillary blood analyte level measurements, (iii) venous blood analyte level measurements, and (iv) ground truth blood analyte levels. The ground truth analyte level may represent the actual analyte level of an animal (e.g., human) body. The ground truth analyte levels cannot be measured directly and are never known. Because ground truth analyte levels are not known, venous blood analyte level measurements are often used as the gold standard analyte level measurements for assessing the accuracy of an analyte monitoring system. However, venous blood analyte level measurements are not practical for continuous analyte monitoring because venous blood analyte level measurements are generally only available in a laboratory setting where a technician can find a vein from which venous blood can be withdrawn. In contrast, capillary blood analyte level measurements can be performed by a patient anywhere (e.g., using a finger-stick blood sample, which is relatively painless and simple when compared to a venous blood draw). In some embodiments, as shown in FIG. 4, the calculated analyte levels, capillary blood analyte level measurements, and venous blood analyte level measurements may each have their own error profiles with respect to the ground truth analyte levels.

As there are no ground truth analyte level measurements, analyte monitoring systems cannot use ground truth analyte level measurements for calibration purposes. In addition, analyte monitoring systems typically do not use venous blood analyte level measurements for calibration purposes because venous blood analyte level measurements are generally available only in laboratory settings. Instead, analyte monitoring systems typically use capillary blood analyte level measurements, which are generally available in real life settings, for calibration purposes.

In some embodiments, the transceiver 101 may calibrate the conversion of sensor measurements to calculated analyte levels using one or more capillary blood analyte level measurements. In some non-limiting embodiments, the calibration using the one or more capillary blood analyte level measurements may minimize the error between calculated blood analyte levels and the capillary blood analyte level measurements. However, due to errors between capillary blood analyte level measurements and venous blood analyte level measurements (see FIG. 4), calibrating the conversation to minimize the error between the calculated blood analyte levels and the capillary blood analyte level measurements may not minimize the error between the calculated blood analyte levels and venous blood analyte level measurements when the accuracy of the calculated blood analyte levels are evaluated in a laboratory setting.

In some alternative embodiments, the transceiver 101 may use one or more capillary blood analyte level measurements to calibrate the conversion of sensor measurements to calculated blood analyte levels but calibrate the conversion to minimize the error between calculated blood analyte levels and estimated venous blood analyte levels (as opposed to minimizing the error between calculated blood analyte levels and the capillary blood analyte level measurements). In some embodiments, the calibration using one or more capillary blood analyte level measurements may include (i) converting the one or more capillary blood analyte level measurements to one or more estimated venous blood analyte levels and (ii) calibrating the conversion of sensor measurements to calculated blood analyte levels to minimize the error between calculated blood analyte levels and the one or more estimated venous blood analyte levels.

Figure 5:
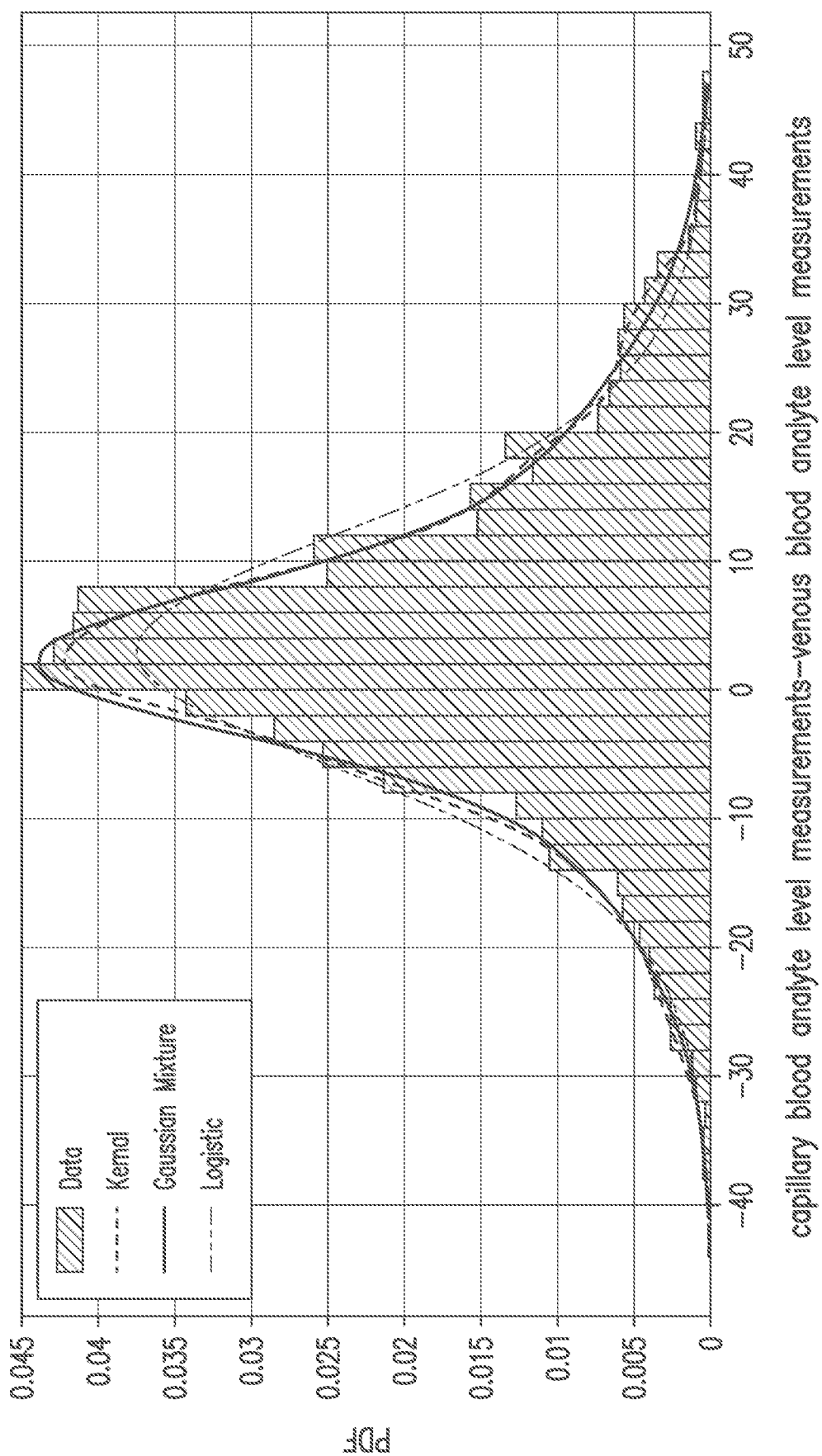
FIG. 5 illustrates an exemplary error model between capillary blood analyte level measurements and venous blood analyte level measurements.

In some non-limiting embodiments, the transceiver 101 may convert the one or more capillary blood analyte level measurements to one or more estimated venous blood analyte levels based on a model of the difference between capillary blood analyte level measurements and venous blood analyte level measurements. FIG. 5 illustrates an exemplary model of the difference between capillary blood analyte level measurements and venous blood analyte level measurements based on experimental data collected during one or more analyte monitoring clinics.

In some embodiments, the transceiver 101 may convert the one or more capillary blood analyte level measurements to one or more estimated venous blood analyte levels based on a cost function that maximizes the likelihood (or minimizes the negative likelihood) of the fit of the error between calculated blood analyte levels and capillary blood analyte level measurements to the error model between the capillary and venous blood analyte level measurements. Non-limiting examples of a cost function that maximizes the likelihood of the fit of the error and a cost function that minimize the negative likelihood of the fit of the error are shown below. In the non-limiting examples, $\theta$ is the cost function, $CGM_\theta$ (t) is a calculated blood analyte level at a time t, and SMBG(t) is a capillary blood analyte level measurement at a time t.

$$\hat{\theta} = \max_{\theta} \sum_{t=1}^{N} w_1 \ln(f_1(e_t)) + w_2 \ln(f_2(e_t))$$

$$\hat{\theta} = \min_{\theta} \sum_{t=1}^{N} -w_1 \ln(f_1(e_t)) - w_2 \ln(f_2(e_t))$$

$$e_t = SMBG(t) - CGM_\theta(t)$$

$$e_t = SMBG(t) - CGM_\theta(t)$$

$$f_j(e_t) = \frac{1}{\sqrt{2\pi\sigma_j^2}} e^{-\frac{(e_t - \mu_j)^2}{2\sigma_j^2}}$$

$$f_j(e_t) = \frac{1}{\sqrt{2\pi\sigma_j^2}} e^{-\frac{(e_t - \mu_j)^2}{2\sigma_j^2}}$$

In some embodiments, the calibration of sensor measurements to calculated blood analyte levels may minimize the error between the calculated blood analyte levels and estimated venous blood analyte levels using capillary blood analyte level measurements, which unlike venous blood analyte measurements can be obtained practically. In some embodiments, the error model may be updated based on one or more new experimental datasets.

Figure 6:
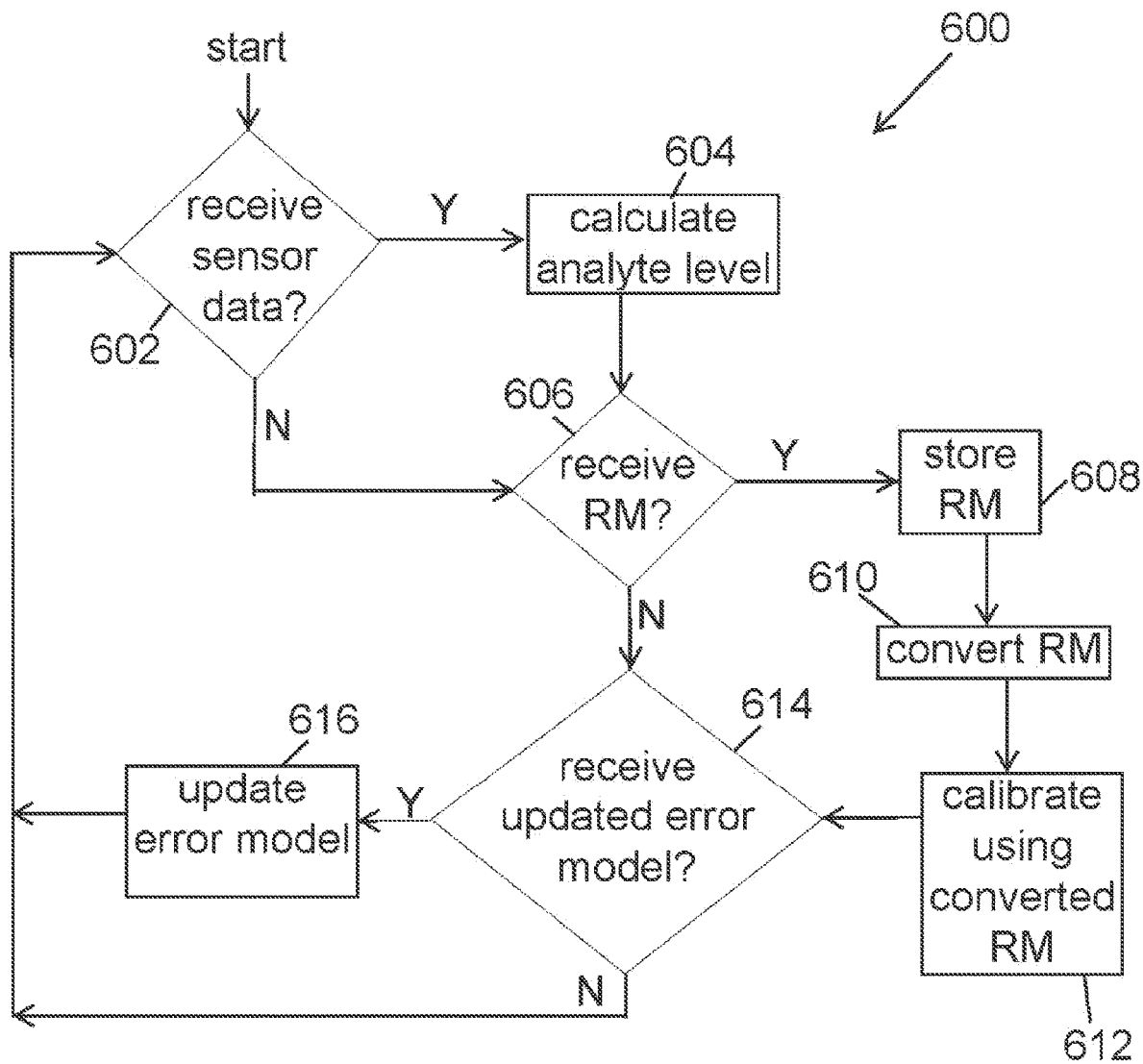
FIG. 6 is a flow chart illustrating a calibration process embodying aspects of the present invention.

FIG. 6 is a flow chart illustrating a calibration process 600 according to some non-limiting embodiments of the invention. In some embodiments, the transceiver 101 may perform one or more steps of the calibration process 600. In some non-limiting embodiments, the computer 920 of the transceiver 101 may perform one or more steps of the calibration process 600.

In some embodiments, as shown in FIG. 6, the calibration process 600 may include a step 602 in which the transceiver 101 determines whether the transceiver 101 has received sensor data (e.g., light and/or temperature measurements) from the sensor 100. In some embodiments, the sensor data may be received following a command (e.g., a measurement command or a read sensor data command) conveyed from the transceiver 101 to the sensor 100. However, this is not required, and, in some alternative embodiments, the sensor 100 may control when sensor data is conveyed to the transceiver 101, or the sensor 100 may continuously convey sensor data to the transceiver 101. In some non-limiting embodiments, the transceiver 101 may receive the sensor data periodically (e.g., every 1, 2, 5, 10, 15, or 20 minutes). In some embodiments, the transceiver 101 may receive the sensor data wirelessly. For example and without limitation, in some non-limiting embodiments, the transceiver 101 may receive the sensor data by detecting modulations in an electromagnetic wave generated by the sensor 100 (e.g., by detecting modulations in the current flowing through the coil 103 of the transceiver 101). However, this is not required, and, in some alternative embodiments, the transceiver 101 may receive the sensor data via a wired connection to the sensor 100. In some non-limiting embodiments, if the sensor has received sensor data, the calibration process 600 may proceed from step 602 to an analyte level calculation step 604. In some non-limiting embodiments, if the transceiver 101 has not received sensor data, the calibration process 600 may proceed from step 602 to a step 606.

In some non-limiting embodiments, the calibration process 600 may include the analyte level calculation step 604. In some embodiments, the step 604 may include calculating an analyte level using a current conversion function and the received sensor data. In some embodiments, the calculated analyte level may be a calculated second medium analyte level (e.g., a calculated blood analyte level). In some embodiments, the analyte level calculation step 604 may include calculating a first medium analyte level (e.g., an ISF analyte level), an M1_ROC (e.g., an ISF_ROC), and the second medium analyte level.

In some non-limiting embodiments, in the analyte level calculation step 604, the transceiver 101 may calculate the first medium analyte level using the received sensor data. In some embodiments, the first medium analyte level may be a measurement of the amount or concentration of the analyte in the first medium (e.g., interstitial fluid) in proximity to the analyte indicator 106. In some non-limiting embodiments, calculation of the first medium analyte level may include, for example and without limitation, some or all of the features described in U.S. application Ser. No. 13/937,871, filed on Jul. 9, 2013, which is incorporated by reference herein in its entirety.

In some non-limiting embodiments, in the analyte level calculation step 604, the transceiver 101 may calculate the M1_ROC using at least the calculated first medium analyte level. In some non-limiting embodiments, the transceiver 101 may calculate the M1_ROC using at least the calculated first medium analyte level and one or more previously calculated first medium analyte levels (e.g., one or more ISF analyte levels calculated using previously received sensor data).

In some non-limiting embodiments, in the analyte level calculation step 604, the transceiver 101 may calculate the second medium analyte level (e.g., blood analyte level) by performing a lag compensation. In some embodiments, the transceiver 101 may calculate the blood analyte level using at least the calculated ISF analyte level and the calculated ISF_ROC. In some non-limiting embodiments, the transceiver 101 may calculate the blood analyte level using the formula $ISF\_ROC/p_2+(1+p_3/p_2)*ISF\_analyte$, where $p_2$ is the analyte diffusion rate, $p_3$ is the analyte consumption rate, ISF_ROC is the calculated ISF_ROC, and ISF_analyte is the calculated ISF analyte level. However, this is not required, and some alternative embodiments may use a different formula for calculating the blood analyte level.

In some embodiments, in step 604, the transceiver 101 may display the calculated analyte level (e.g., calculated blood analyte level). In some non-limiting embodiments, the transceiver 101 may display the calculated analyte level by conveying it to the display device 105 for display. In some non-limiting embodiments, the transceiver 101 may additionally or alternatively display the calculated analyte level by display it on a display (e.g., display 924) of the transceiver 101.

In some non-limiting embodiments, the calibration process 600 may include the step 606 in which the transceiver 101 determines whether the transceiver 101 has received a reference measurement. The reference measurement may be a reference analyte measurement. In some non-limiting embodiments, the reference measurement may be a capillary blood analyte measurement (e.g., an SMBG measurement) obtained from, for example and without limitation, a fingerstick blood sample. In some embodiments, the transceiver 101 may receive reference measurements periodically or on an as-needed basis. In some embodiments, the transceiver 101 may receive the reference measurement from the display device 105 (e.g., using the display interface of the transceiver 101). In some non-limiting embodiments, the transceiver 101 may cause the display device 105 to prompt a user for the reference measurement, and, in response, the user may enter the reference measurement into the display device 105. In some alternative embodiments, the transceiver 101 may prompt a user for the reference measurement, and, in response, the user may enter the reference measurement directly into the transceiver 101.

In some embodiments, if the transceiver 101 has not received a reference measurement, the calibration process 600 may proceed to a step 614. In some embodiments, if the transceiver 101 has received a reference measurement, the calibration process 600 may proceed to a step 608.

In some non-limiting embodiments, the calibration process 600 may include a step 608 in which the reference measurement is stored, for example, in a calibration point memory (e.g., a circular buffer). In some embodiments, the reference measurement may be stored in the calibration point memory with a corresponding reference time stamp. In some embodiments, the calibration process 600 may proceed from step 608 to a step 610.

In some embodiments, the calibration process 600 may include a step 610 in which the transceiver 101 converts the received reference measurement into an estimated analyte level. In some embodiments, the received reference measurement may be a capillary blood analyte measurement, and the estimated analyte level may be an estimated venous blood analyte level. In some embodiments, the conversion of the reference measurement into the estimated analyte level may be carried out using a model (e.g., error model) of differences between capillary blood analyte level measurements and venous blood analyte level measurements. In some embodiments, the conversion of the reference measurement into the estimated analyte level may be carried out using a cost function that maximizes the likelihood of a fit of the error between calculated analyte levels and capillary blood analyte level measurements to the model of the differences between the capillary blood analyte level measurements and the venous blood analyte level measurements. In some alternative embodiments, the conversion of the reference measurement into the estimated analyte level may be carried out using a cost function minimizes the negative likelihood of a fit of the error between calculated analyte levels and capillary blood analyte level measurements to the model of the differences between the capillary blood analyte level measurements and the venous blood analyte level measurements. In some non-limiting embodiments, the transceiver 101 may store the reference measurement (e.g., in a calibration point memory).

In some embodiments, the calibration process 600 may include a calibration step 612 in which the transceiver 101 updates the conversion function used to calculate second medium (e.g., blood) analyte levels from the received sensor data. In some embodiments, the transceiver 101 may update the conversion function using at least the estimated analyte level (e.g., the estimated venous blood analyte level) as a calibration point. In some non-limiting embodiments, the transceiver 101 may update the conversion function using the estimated analyte level and one or more additional estimated analyte levels, which were converted from one or more previously received reference measurements, as calibration points. In some non-limiting embodiments, the transceiver 101 may assign weights to the estimated analyte levels (e.g., based on how old the estimated analyte levels are). In some embodiments, the updated conversion function minimizes the error between analyte levels calculated using the updated conversion function and one or more estimated analyte levels. In some non-limiting embodiments, the updated conversion function may have one or more updated lag parameters. In some non-limiting embodiments, one or more updated lag parameters may include one or more of an updated analyte diffusion rate ($p_2$) and an updated analyte consumption rate ($p_3$). In some embodiments, the calibration process 600 may proceed from step 612 to step 602 (or to step 614 as shown in FIG. 6), and the transceiver 101 may use the updated conversion function to calculate analyte levels from subsequent sensor data.

In some non-limiting embodiments, the calibration process 600 may include the step 614 in which the transceiver 101 determines whether the transceiver 101 has received an updated error model. In some non-limiting embodiments, the transceiver 101 may receive an updated error model from the display device 105 (e.g., via the display interface of the transceiver 101). In some embodiments, the error model may have been updated based on one or more new experimental datasets. In some embodiments, the updated error model may model differences between capillary blood analyte level measurements and venous blood analyte level measurements. In some embodiments, if the transceiver 101 has not received an updated error model, the calibration process 600 may proceed to step 602. In some embodiments, if the transceiver 101 has received a reference measurement, the calibration process 600 may proceed to a step 616.

In some non-limiting embodiments, the calibration process 600 may include the step 616 in which the transceiver 101 replaces the error model used to convert the received reference measurements (e.g., capillary blood analyte measurements) into estimated analyte levels (e.g., estimated venous blood analyte levels) with the received updated error model. In some embodiments, the calibration process 600 may proceed from step 616 to step 602, and the transceiver 101 may use the updated error model to convert subsequent reference measurements into estimated analyte levels.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although the invention is described above in the context of an analyte monitoring system that calculates blood analyte levels indirectly using measurements of analyte levels in interstitial fluid, the invention is applicable to any monitoring system that calculates levels in a first medium using measurements of levels in a second medium.

What is claimed is:

1. A system comprising:
an analyte sensor;
a transceiver configured to:
receive first sensor data from the analyte sensor;
calculate a first analyte level using a conversion function and the first sensor data;
receive a reference analyte measurement, wherein the reference analyte measurement is a capillary blood analyte measurement;
convert the reference analyte measurement into an estimated analyte level, wherein the estimated analyte level is an estimated venous blood analyte level;
update the conversion function using the estimated analyte level as a calibration point;
receive second sensor data from the analyte sensor; and
use the updated conversion function and the second sensor data to calculate a second analyte level.

2. The system of claim 1, wherein the updated conversion function minimizes the error between analyte levels calculated using the updated conversion function and estimated venous blood analyte levels.

3. The system of claim 1, wherein the reference analyte measurement is a self-monitoring blood glucose (SMBG) measurement obtained from a finger-stick blood sample.

4. The system of claim 1, wherein the conversion of the reference analyte measurement into the estimated analyte level is based on a model of differences between capillary blood analyte level measurements and venous blood analyte level measurements.

5. The system of claim 4, wherein the conversion of the reference analyte measurement into the estimated analyte level is based on a cost function that maximizes the likelihood of a fit of the error between calculated analyte levels and capillary blood analyte level measurements to the model of the differences between the capillary blood analyte level measurements and the venous blood analyte level measurements.

6. The system of claim 4, wherein the conversion of the reference analyte measurement into the estimated analyte level is based on a cost function minimizes the negative likelihood of a fit of the error between calculated analyte levels and capillary blood analyte level measurements to the model of the differences between the capillary blood analyte level measurements and the venous blood analyte level measurements.

7. The system of claim 1, wherein the first analyte level is a second medium analyte level, and calculating the first analyte level using the conversion function and the first sensor data comprises:
calculating a first medium analyte level using at least the first sensor data;
calculating a first medium analyte level rate of change using at least the first medium analyte level; and
calculating the second medium analyte level using at least the first medium analyte level and first medium analyte level rate of change.

8. The system of claim 7, wherein the first medium is interstitial fluid, and the second medium is blood.

9. The system of claim 1, wherein the first sensor data includes light and temperature measurements.

10. The system of claim 1, wherein the transceiver is further configured to:
receive an updated error model;
receive a second reference analyte measurement;
convert the second reference analyte measurement into a second estimated analyte level using the updated error model;
update the conversion function using the second estimated analyte level as a calibration point;
receive third sensor data from the analyte sensor; and
use the twice updated conversion function and the third sensor data to calculate a third analyte level.

11. A method comprising:
using a transceiver to receive first sensor data from an analyte sensor;
using the transceiver to calculate a first analyte level using a conversion function and the first sensor data;
using the transceiver to receive a reference analyte measurement, wherein the reference analyte measurement is a capillary blood analyte measurement;

using the transceiver to convert the reference analyte measurement into an estimated analyte level, wherein the estimated analyte level is an estimated venous blood analyte level;

using the transceiver to update the conversion function using the estimated analyte level as a calibration point;

using the transceiver to receive second sensor data from the analyte sensor; and using the transceiver to calculate a second analyte level using the updated conversion function and the second sensor data.

12. The method of claim 11, wherein the updated conversion function minimizes the error between analyte levels calculated using the updated conversion function and estimated venous blood analyte levels.

13. The method of claim 11, wherein the reference analyte measurement is a self-monitoring blood glucose (SMBG) measurement obtained from a finger-stick blood sample.

14. The method of claim 11, wherein the conversion of the reference analyte measurement into the estimated analyte level is based on a model of differences between capillary blood analyte level measurements and venous blood analyte level measurements.

15. The method of claim 14, wherein the conversion of the reference analyte measurement into the estimated analyte level is based on a cost function that maximizes the likelihood of a fit of the error between calculated analyte levels and capillary blood analyte level measurements to the model of the differences between the capillary blood analyte level measurements and the venous blood analyte level measurements.

16. The method of claim 14, wherein the conversion of the reference analyte measurement into the estimated analyte level is based on a cost function minimizes the negative likelihood of a fit of the error between calculated analyte levels and capillary blood analyte level measurements to the model of the differences between the capillary blood analyte level measurements and the venous blood analyte level measurements.

17. The method of claim 11, wherein the first analyte level is a second medium analyte level and calculating the first analyte level using the conversion function and the first sensor data comprises:

calculating a first medium analyte level using at least the first sensor data;

calculating a first medium analyte level rate of change using at least the first medium analyte level; and calculating the second medium analyte level using at least the first medium analyte level and first medium analyte level rate of change.

18. The method of claim 17, wherein the first medium is interstitial fluid, and the second medium is blood.

19. The method of claim 11, wherein the first sensor data includes light and temperature measurements.

20. The method of claim 11, further comprising:

using the transceiver to receive an updated error model;

using the transceiver to receive a second reference analyte measurement;

using the transceiver to convert the second reference analyte measurement into a second estimated analyte level using the updated error model;

using the transceiver to update the conversion function using the second estimated analyte level as a calibration point;

using the transceiver to receive third sensor data from the analyte sensor; and using the transceiver to use the twice updated conversion function and the third sensor data to calculate a third analyte level.

21. A transceiver comprising:

a sensor interface configured to receive first sensor data and second sensor data from the analyte sensor;

a display interface configured to receive a reference analyte measurement from a display device, wherein the reference analyte measurement is a capillary blood analyte measurement; and a computer comprising a non-transitory and a processor, wherein the computer is configured to:

use a conversion function and the first sensor data to calculate a first analyte level;

convert the reference analyte measurement into an estimated analyte level, wherein the estimated analyte level is an estimated venous blood analyte level;

update the conversion function using the estimated analyte level as a calibration point; and use the updated conversion function and the second sensor data to calculate a second analyte level.

22. The transceiver of claim 21, wherein the updated conversion function minimizes the error between analyte levels calculated using the updated conversion function and estimated venous blood analyte levels.

23. The transceiver of claim 21, wherein the reference analyte measurement is a self-monitoring blood glucose (SMBG) measurement obtained from a finger-stick blood sample.

24. The transceiver of claim 21, wherein the conversion of the reference analyte measurement into the estimated analyte level is based on a model of differences between capillary blood analyte level measurements and venous blood analyte level measurements.

25. The transceiver of claim 24, wherein the conversion of the reference analyte measurement into the estimated analyte level is based on a cost function that maximizes the likelihood of a fit of the error between calculated analyte levels and capillary blood analyte level measurements to the model of the differences between the capillary blood analyte level measurements and the venous blood analyte level measurements.

26. The transceiver of claim 24, wherein the conversion of the reference analyte measurement into the estimated analyte level is based on a cost function minimizes the negative likelihood of a fit of the error between calculated analyte levels and capillary blood analyte level measurements to the model of the differences between the capillary blood analyte level measurements and the venous blood analyte level measurements.

27. The transceiver of claim 21, wherein the first analyte level is a second medium analyte level, and using the conversion function and the first sensor data to calculate the first analyte level comprises:

calculating a first medium analyte level using at least the first sensor data;

calculating a first medium analyte level rate of change using at least the first medium analyte level; and calculating the second medium analyte level using at least the first medium analyte level and first medium analyte level rate of change.

28. The transceiver of claim 27, wherein the first medium is interstitial fluid, and the second medium is blood.

29. The transceiver of claim 21, wherein the first sensor data includes light and temperature measurements.

30. The transceiver of claim 21, wherein:
the sensor interface is further configure to receive third sensor data from the analyte sensor;
the display interface is further configured to receive an updated error model and a second reference analyte measurement; and
the computer is further configured to:
   convert the second reference analyte measurement into a second estimated analyte level using the updated error model;
   update the conversion function using the second estimated analyte level as a calibration point;
   receive third sensor data from the analyte sensor; and
   use the twice updated conversion function and the third sensor data to calculate a third analyte level.

* * * * *